(12) United States Patent
Geiger et al.

(10) Patent No.: US 7,991,211 B2
(45) Date of Patent: Aug. 2, 2011

(54) METHOD AND SYSTEM FOR GUIDED TWO DIMENSIONAL COLON SCREENING

(75) Inventors: Bernhard Geiger, Cranbury, NJ (US); Sandra Sudarsky, Bedminster, NJ (US)

(73) Assignee: Siemens Aktiengesellschaft, Munich ( * ) Notice: Subject to any disclaimer, the term of this patent is extended or adjusted under 35 U.S.C. 154(b) by 883 days.

(21) Appl. No.: 11/968,308

(22) Filed: Jan. 2, 2008

(65) Prior Publication Data
US 2008/0175459 A1 Jul. 24, 2008

Related U.S. Application Data

(60) Provisional application No. 60/885,955, filed on Jan. 22, 2007.

(51) Int. Cl.
*G06K 9/00* (2006.01)
*A61B 5/05* (2006.01)

(52) U.S. Cl. .................. 382/131; 382/154; 600/425

(58) Field of Classification Search .......... 382/100, 382/128, 129, 130, 131, 132, 133, 134, 154, 382/168, 173, 181, 199, 232, 254, 256, 274, 382/276, 285, 305, 312; 600/407, 103, 425; 378/2, 4, 6, 21, 50
See application file for complete search history.

(56) References Cited

U.S. PATENT DOCUMENTS

| 7,792,565 | B2 * | 9/2010 | Vining ................... 600/407 |
| 7,853,058 | B2 * | 12/2010 | Gauldie et al. ............ 382/128 |
| 2005/0152588 | A1 * | 7/2005 | Yoshida et al. ............ 382/128 |
| 2007/0071297 | A1 * | 3/2007 | Geiger et al. .............. 382/128 |
| 2007/0165928 | A1 * | 7/2007 | Yoshida et al. ............ 382/128 |
| 2008/0194946 | A1 * | 8/2008 | Summers et al. ........... 600/425 |
| 2009/0048482 | A1 * | 2/2009 | Hong et al. ............... 600/103 |

* cited by examiner

*Primary Examiner* — Seyed Azarian
(74) *Attorney, Agent, or Firm* — Donald B. Paschburg

(57) ABSTRACT

A method and apparatus for guiding image reading for colon screening, includes calculating a centerline for a colon; scrolling through a succession of two dimensional (2D) cross-sectional images of a colon in respective image planes, such that a current image plane includes a respective current focus point formed by an intersection of the centerline with the current image plane. The method further includes performing a three-dimensional (3D) region growing process for growing a region of a suitable given thickness around a current seed point in a current image plane, the current seed point being at the respective current focus point in the current image plane, such that the region growing "floods" folds within a prescribed distance from the current seed point such that part of the region intersects the current image plane. Portions of the region intersecting the current image plane that meets at least one of conditions (A) and (B) are removed from consideration where: condition (A) includes the region intersecting the given current image plane containing a further connected component not containing the current seed point, and containing a further intersection of the image plane with the centerline other than the current seed point, and condition (B) includes the further connected component exhibiting a larger area than that exhibited by a connected component containing the current seed point; and marking remaining portions of the region intersecting the current image plane, not removed from consideration, as seen areas.

25 Claims, 7 Drawing Sheets

1

METHOD AND SYSTEM FOR GUIDED TWO DIMENSIONAL COLON SCREENING

CROSS-REFERENCE TO RELATED APPLICATIONS AND PRIORITY

Specific reference is hereby made to provisional Application No. 60/885,955, entitled Improvement for unseen areas in guided two dimensional colon screening, filed Jan. 22, 2007 in the names of Bernhard Geiger and Sandra Sudarsky, the inventors in the present application, and of which the benefit of priority is claimed and whereof the disclosure is hereby incorporated herein by reference in its entirety.

Reference is also made to patent application Ser. No. 11/438,499 entitled METHOD AND SYSTEM FOR GUIDED TWO DIMENSIONAL COLON SCREENING, filed on May 22, 2006 in the names of Bernhard Geiger and Sandra Sudarsky, the inventors in the present application, and whereof the disclosure is hereby incorporated herein by reference in its entirety; and to patent application Ser. No. 11/438,617 entitled METHOD AND SYSTEM FOR DISPLAYING UNSEEN AREAS IN GUIDED TWO DIMENSIONAL COLON SCREENING, filed on May 22, 2006 in the names of Bernhard Geiger and Sandra Sudarsky, the inventors in the present application, and whereof the disclosure is hereby incorporated herein by reference in its entirety.

FIELD OF THE INVENTION

The present application relates generally to computer vision and imaging systems and, more particularly, to computerized imaging as applied to guided two dimensional colon screening.

BACKGROUND OF THE INVENTION

Virtual colonoscopy is a noninvasive technique for human colon cancer screening. Computed tomography (CT) or Magnetic resonance (MR) techniques are used to generate high-resolution cross-sectional images of the inner surface of the colon. The techniques are presently of importance in the field of medicine Both CT and MR colonography generate a large number of images that must be interpreted by a radiologist for the presence of polyps; see Arie E. Kaufman, Sarang Lakare, Kevin Kreeger, Ingmar Bitter, Virtual Colonoscopy, Communications of the ACM, vol 48, No. 2, pp. 37-41, 2005; and the paper by Macari, Lavelle, Berman, and Megibow cited in the next paragraph.

Commonly used methods to examine these datasets include slice-by-slice viewing, referred to as primary 2-dimensional (2D) reading and virtual flythroughs referred to as primary 3-dimensional (3D) reading. There appears to be little agreement in the literature as to which method results in the greatest rate of polyp detection; see Hara A. K., Johnson C. D., Reed J. E., Ehman R. L., Ilsrtup D. M., Colorectal polyp detection with CT Colonography, two-versus three dimensional techniques, Radiology, 1996, 200:49-54; Macari M, Milano A, Lavelle M, Berman P, Megibow A J. Comparison of time-efficient CT colonography with two- and three-dimensional colonic evaluation for detecting colorectal polyps, AJR Am J Roentgenol. 2000, 174:1543-9; Macari M, Lee J, Garcia Figueiras R, Megibow A, Bennett G, Badd J, Primary 2D versus 3D Interpretation Techniques Using Thin Section Multi-Detector Row CT Colonography (CTC), RSNA, 2004.

A number of techniques have been proposed to facilitate 3D reading. Most of these techniques automate the navigation process by calculating the colonic centerline; see for example, U.S. patent application Ser. No. 10/842,972, filed May 11, 2004 in the name of Boissonnat, Jean-Daniel and Geiger, Bernhard and entitled METHOD AND APPARATUS FOR FAST AUTOMATIC CENTERLINE EXTRACTION FOR VIRTUAL ENDOSCOPY whereof the disclosure is incorporated herein by reference; and Robert J. T. Sadleir, Paul F. Whelan, Colon Centerline Calculation for CT Colonography using Optimised 3D Topological Thinning, 1st International Symposium on 3D Data Processing Visualization and Transmission (3DPVT'02), pp. 800-804, 2002; I. Bitter, M. Sato, M. Bender, A. Kaufman, M. Wan, CEASAR: A Smooth, Accurate and Robust Centerline Extraction Algorithm, In Proc. IEEE Visualisation, 2000; R. Chiou, A. Kaufman, Z. Liang, L. Hong, and M. Achniotou, Interactive Fly-Path Planning Using Potential Fields and Cell Decomposition for Virtual Endoscopy," IEEE Trans Nuclear Sciences, vol. 46, no. 4, pp. 1045-1049, 1999; and Samara Y., Fiebich M., Dachman A. H., Kuniyoshi J. K., Doi K., Hoffmann K. R., Automated calculation of the centerline of the human colon on CT images, Acad Radiol. 1999 June; 6(6): 352-9.

Other techniques automate the navigation process by computing the longest ray cast along the view direction. See, for example, U.S. patent application Ser. No. 10/322,326, filed Dec. 18, 2002 in the name of B. Geiger, and entitled AUTOMATIC NAVIGATION FOR VIRTUAL ENDOSCOPY, whereof the disclosure is incorporated herein by reference.

Another valuable help for 3D reading is the availability of techniques to get a map of colon wall patches that have not been observed during flythrough. Frequently, such areas are between deep Haustral folds. Such techniques have been proposed by, for example, F. M. Vos et. al. "A new visualization method for virtual colonoscopy", Lecture Notes in Computer Science, vol. 2208, 2001. However, these techniques are limited to 3D flythrough.

BRIEF SUMMARY OF THE INVENTION

A method and apparatus for guiding image reading for colon screening includes calculating a centerline for a colon; scrolling through a succession of two dimensional (2D) cross-sectional images of a colon in respective image planes, such that a current image plane includes a respective current focus point, formed by an intersection of the centerline with the current image plane, also referred to as a point of intersection. The method further includes performing a three-dimensional (3D) region growing process for growing a region of a suitable given thickness around a current seed point in a current image plane, the current seed point being at the respective current focus point in the current image plane, such that the region growing "floods" folds within a prescribed distance from the current seed point such that part of the region intersects the current image plane. Portions of the region intersecting the current image plane that meets at least one of conditions (A) and (B) are removed from consideration where condition (A) comprises the region intersecting the given current image plane containing a further connected component not containing the current seed point, and containing a further intersection of the image plane with the centerline other than the current seed point, and condition (B) comprises the further connected component exhibiting a larger area than that exhibited by a connected component containing the current seed point; and marking remaining portions of the region intersecting the current image plane, not removed from consideration, as seen areas.

In accordance with an aspect of the invention, a method for guiding image reading for colon screening comprises calculating a centerline for a colon to be screened; scrolling through a succession of two dimensional (2D) cross-sectional images of a colon in respective image planes, such that a current image plane includes a respective current focus point formed by an intersection of the centerline with the current image plane; performing a three-dimensional (3D) region growing process for growing a region of a suitable given thickness around a current seed point in a current image plane, the current seed point being at the respective current focus point in the current image plane, such that the region growing floods any folds within a prescribed distance from the current seed point and such that part of the region intersects the current image plane; and marking portions of the region intersecting the current image with a first mark.

In accordance with another aspect of the invention, the step of performing a 3D region growing process comprises flooding Haustral fold areas within a given range of a respective current seed point.

In accordance with another aspect of the invention, a method for guiding image reading includes marking any of the portions marked with the first mark as "seen areas".

In accordance with another aspect of the invention, a method for guiding image reading includes calculating a total colon surface area by calculating segmentation and colon surface for the colon; and calculating unseen areas of the colon surface by subtracting the seen areas from the total colon area.

In accordance with another aspect of the invention, a method for guiding image reading includes marking as "not seen" any of the portions marked with the first mark that meet a given criterion, wherein the criterion comprises at least one of:
(A) the region intersecting the given current image plane contains a further connected component not containing the current seed point, and contains a further intersection of the image plane with the centerline other than the current seed point, and (B) the further connected component exhibits a larger area than that exhibited by a connected component containing the current seed point; and marking remaining portions of the region intersecting the current image plane, not removed from consideration, with a second mark as "seen areas".

In accordance with another aspect of the invention, a method for guiding image reading includes calculating a total colon surface area by calculating segmentation and colon surface for the colon; and calculating unseen areas of the colon surface by subtracting the seen areas from the total colon area.

In accordance with another aspect of the invention, a method for guiding image reading includes the scrolling through a succession of two dimensional (2D) cross-sectional images of a colon in respective image planes comprises scrolling such that a current image plane includes a respective current focus point formed by an intersection of a projection of the centerline with the current image plane.

In accordance with another aspect of the invention, a method for guiding image reading includes (a) calculating a centerline for a colon; (b) scrolling through a succession of two dimensional (2D) cross-sectional images of a colon in respective image planes, such that a current image plane includes a respective current focus point formed by an intersection of the centerline with the current image plane; (c) performing a three-dimensional (3D) region growing process for growing a region of a suitable given thickness around a current seed point in the current image plane, the current seed point being at the respective current focus point in the current image plane, such that the region growing "floods" folds within a prescribed distance from the current seed point such that part of the region intersects the current image plane; (d) marking as "not seen" any portions of the region intersecting the current image plane that meet at least one of conditions (A) and (B), wherein condition (A) comprises the region intersecting the given current image plane containing a further connected component not containing the current seed point, and containing a further intersection of the image plane with the centerline other than the current seed point, and condition (B) comprises the further connected component exhibiting a larger area than that exhibited by a connected component containing the current seed point; and (e) marking remaining portions of the region intersecting the current image plane, not marked as "not seen", as "seen areas".

In accordance with another aspect of the invention, a method for guiding image reading includes scrolling such that a current image plane includes a respective current focus point formed by an intersection of a projection of the centerline with the current image plane.

In accordance with another aspect of the invention, a method for guiding image reading includes a step (e') calculating a total colon surface area by calculating segmentation and colon surface for the colon; and a step (e") calculating a total of unseen areas of the colon surface by subtracting the seen areas from the total colon area.

In accordance with another aspect of the invention, a method for guiding image reading includes step (c) comprising flooding Haustral fold areas within a given range of a respective current seed point.

In accordance with another aspect of the invention, a method for guiding image reading includes scrolling through a succession of two dimensional (2D) cross-sectional images of a colon in respective image planes, such that a first current (cross-sectional) image plane includes a respective first current focus point formed by an intersection of the centerline with the first current image plane; marking the first respective current focus point in a first color; scrolling to a next current image plane in a respective next current image plane including a next respective current focus point; marking the next respective current focus point in the first color; projecting the first focus point onto the next current cross-sectional image to form a projection thereof; and marking the projection in a second color.

In accordance with another aspect of the invention, a method for guiding image reading includes steps for finding unseen areas in an image for colon screening, comprising calculating a centerline for a colon; scrolling through a succession of two dimensional (2D) cross-sectional images of the colon in respective image planes, such that a current image plane includes a respective current focus point formed by an intersection of the centerline with the current image plane until, in the event of the colon exhibiting a bend such that the centerline exhibits a bend ahead of the scrolling, a critical image plane is reached, including a critical focus point, wherein further scrolling to a next plane causes the centerline to no longer intersect the next plane by veering away due to the bend; projecting a guide line from the critical focus point in a substantially perpendicular direction to the critical image plane; and scrolling through a further succession of 2D cross-sectional images of the colon in further respective image planes beyond the critical image plane, such that a further current image plane includes a further respective focus point formed by an intersection of the guide line with the further current image plane.

In accordance with another aspect of the invention, a method for guiding image reading includes the step of scrolling through a further succession of 2D cross-sectional images comprises reversing the direction of scrolling once a wall of the colon is reached.

In accordance with another aspect of the invention, a system for guiding image reading for colon screening comprises a memory device for storing a program and other data; and a processor in communication with the memory device, the processor being operative with the program to perform foregoing steps in accordance with principles of the present invention.

In accordance with another aspect of the invention, a computer program product comprises a computer useable medium having computer program logic recorded thereon for program code for guiding image reading for colon screening, comprising foregoing steps in accordance with principles of the present invention.

BRIEF DESCRIPTION OF THE DRAWING

The invention, including the foregoing aspects and other aspects will be more fully understood from the detailed description which follows and the Drawing, in which.

DETAILED DESCRIPTION OF THE INVENTION

Figure 1:
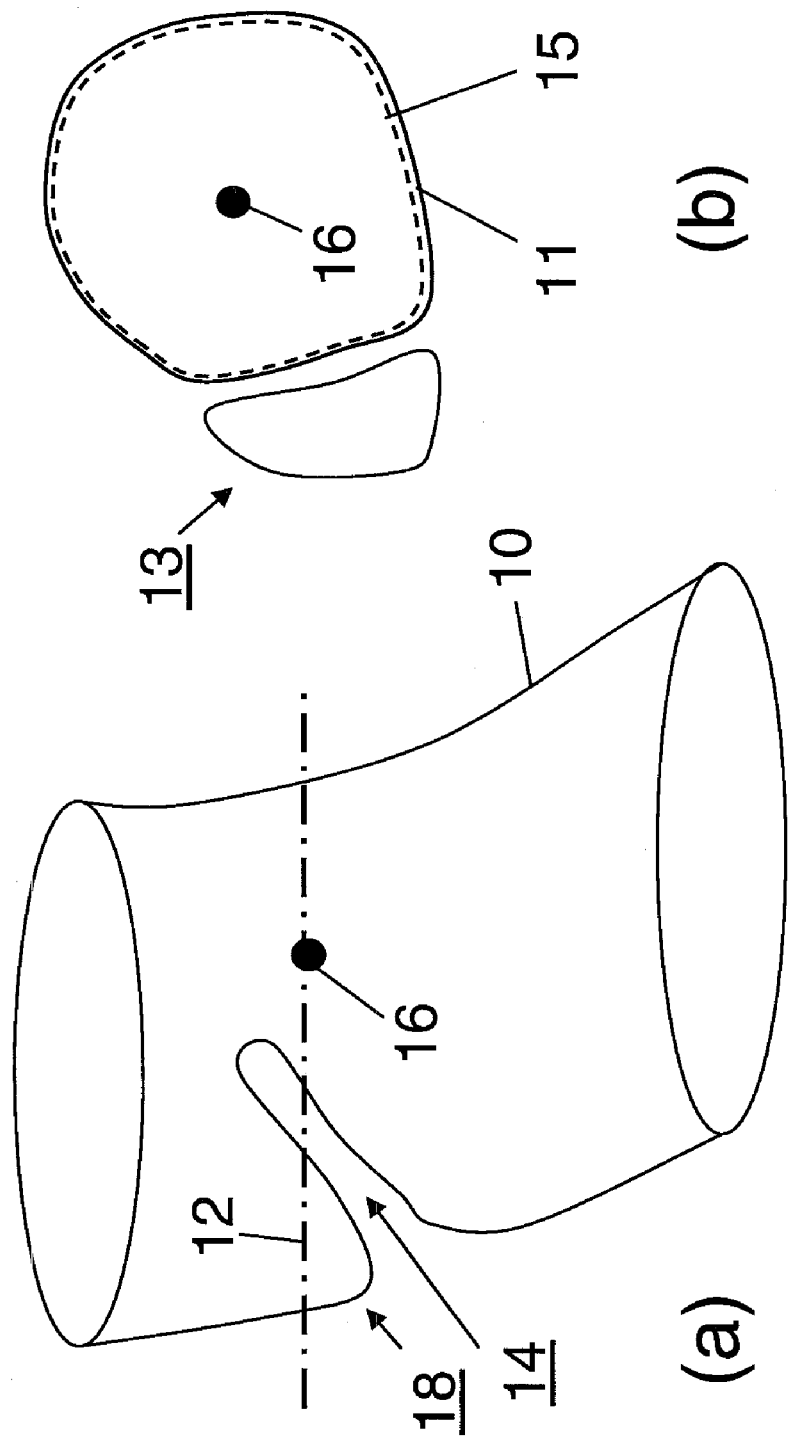
FIG. 1 shows an exemplary configuration in a virtual colonoscopy with seed growing and a Haustral fold illustrating one of the problems solved by the present invention and helpful to a fuller understanding of the present invention.

It is herein recognized that very little has been proposed to facilitate slice-by-slice viewing. The convoluted structure typical of the colon makes slice-based visual inspection quite difficult. Generally, the radiologist must typically utilize manual control to browse through hundreds of two-dimensional images in search of polyps. Since the slice-based view does not provide a contiguous presentation of the inner surface of the colon, the radiologist must scroll up and down the axial images following a mental picture of the anatomical structure. An object of the present invention is to provide a method for reducing the difficulty of performing accurate slice-based visual inspection.

A basic technique for detecting colorectal polyps in CT data is to use axial images, by starting at the rectum, and carefully scrolling up and down through the images, following the colon. Since the colon is generally heavily convoluted, the scroll direction typically has to be repeatedly reversed. It is herein recognized that an important challenge for the radiologist is not to get distracted by the presence of other air filled structures in the images, such as the small intestine or other loops of the colon, which can cause pretermission or inadvertent skipping over of portions of the colon in the inspection process within which anomalies such as polyps may thus remain unobserved and undetected. An object of the present invention is to reduce any chance of inadvertent skipping over of portions of the colon in the inspection process.

By way of an example, a colon may exhibit portions looping up and down such that an image plane may intersect the colon in a plurality of places, which will appear as more or less circular cross-sections on the image plane. Beginning at an initial point, for example at the rectal end of the colon, the radiologist can follow a series of cross-sectional images of a first ascending segment of the colon which will appear on a succession of image planes at increasing distances from the initial point. Let the first ascending segment exhibit an inverted U arch, forming a ∩-shaped segment, and continue as a descending segment. The radiologist will then see two cross-sectional images on the image plane, corresponding to the ascending and descending segments, respectively. Also, other disjoint cross-sectional images corresponding to other loops of the colon may be present on the image plane so that a total of, for example, four cross-sectional images appear on the image plane.

As the image plane scrolls up, out of the four visible cross-sectional images, the radiologist will concentrate on the ascending segment as the currently observed portion. At some point, the image plane will reach above the arch, and the cross-sectional images of the ascending and descending segments will disappear. From a knowledge of anatomy, the radiologist will understand that this is attributable to the image plane being located above the arch and that somewhere there is a continuation of the colon as the descending segment.

The image plane now scrolls down, and the radiologist must focus on the cross-sectional image of the descending segment, which is one of four cross-sectional images on the image plane. Should the radiologist through error or inadvertence at some point focus on another, incorrect cross-sectional image, a significant part might be missed, and/or valuable time lost in order to backtrack from the error. In the real world, there will typically be many more folds and the small intestine will be present in the region, which will increase the chances for error, especially for a less experienced radiologist.

It is known that an approximate centerline through the colon can be provided. For example, an approximate centerline can be calculated as described in the above-cited papers by J. T. Robert et al.; I. Bitter et al.; R. Chiou et al.; Y. Samara et al.; and in the above-referenced United States patent application entitled METHOD AND APPARATUS FOR FAST AUTOMATIC CENTERLINE EXTRACTION FOR VIRTUAL ENDOSCOPY.

In the aforementioned patent application Ser. No. 11/438, 499 entitled METHOD AND SYSTEM FOR GUIDED TWO DIMENSIONAL COLON SCREENING, the present inventors disclose a method and system for guiding imaging reading for colon screening which includes scrolling through a succession of two dimensional (2D) cross-sectional images of a colon in respective image planes. A point of intersection with a current image plane with the centerline of the colon is marked in a first color in the current cross-sectional image. As the scrolling proceeds and a new current cross-sectional image in a respective image plane is observed, a new point of intersection is marked in the current cross-sectional image in the first color and the prior point of intersection is projected onto the new current cross-sectional image and marked in a second color. Reference is made to the patent for further details.

In the aforementioned patent application Ser. No. 11/438,617 entitled METHOD AND SYSTEM FOR DISPLAYING UNSEEN AREAS IN GUIDED TWO DIMENSIONAL COLON SCREENING, the present inventors disclosed a method and system for displaying unseen areas in guided two dimensional (2D) colon screening by using a 2D sweeping plane and performing a 2D region growing in the plane, using the current point of focus as a seed point. The method includes calculating segmentation and colon surface for a colon; calculating a centerline for the colon; designating as a current focus point a current point of intersection of a current portion of the centerline and a current cross-sectional image of a colon in a current image plane; and extracting a colon surface portion in a connected colon component containing the current focus point; and marking voxels of the colon surface portion as a "seen" area. Unseen areas of the colon surface are calculated by subtracting seen areas from the total colon area of observation. The unseen areas may then be displayed. The patent also refers to performing scrolling to yet further cross-sectional images on yet further image planes and repeating the foregoing steps, mutatis mutandis; then projecting foregoing points of intersection on each successive current image plane; and if the separation distance between a projected point and the current point of intersection is within a given criterion, that projected point is displayed and otherwise not. Reference is made to the patent for further details.

The inventors herein have recognized that, by the use of the foregoing method in certain particular circumstances, small unseen areas are likely to result because of folds that are typically oriented at an oblique angle with respect to the 2D cutting or section plane. FIG. 1 of the present application shows in diagrammatic fashion such a configuration including a Haustral fold, wherein, in FIG. 1(a), 10 represents a wall of a section of a colon in which a Haustral fold 14 is present. A cutting or image plane 12 yields a first section shown as 11 in FIG. 1(b) and point 16 in FIG. 1(a) and FIG. 1(b) represents a point of intersection between image plane 12 and the centerline (not shown) of the section of the colon. Haustral fold 14 causes a portion of the colon to form a second section 13 as shown in FIG. 1(b), not containing an intersection of the centerline with cutting plane 12 and separated from the first section view 11.

A region growing from the seed point at point 16 in the image plane would only result in the dashed contour 15 to be marked as "seen", and would not contain a contour in the section 13 corresponding to portion 18 behind the Haustral fold. However, such folds are very close to the center of focus, and should be covered in the 2D reading process in one pass.

Figure 2:
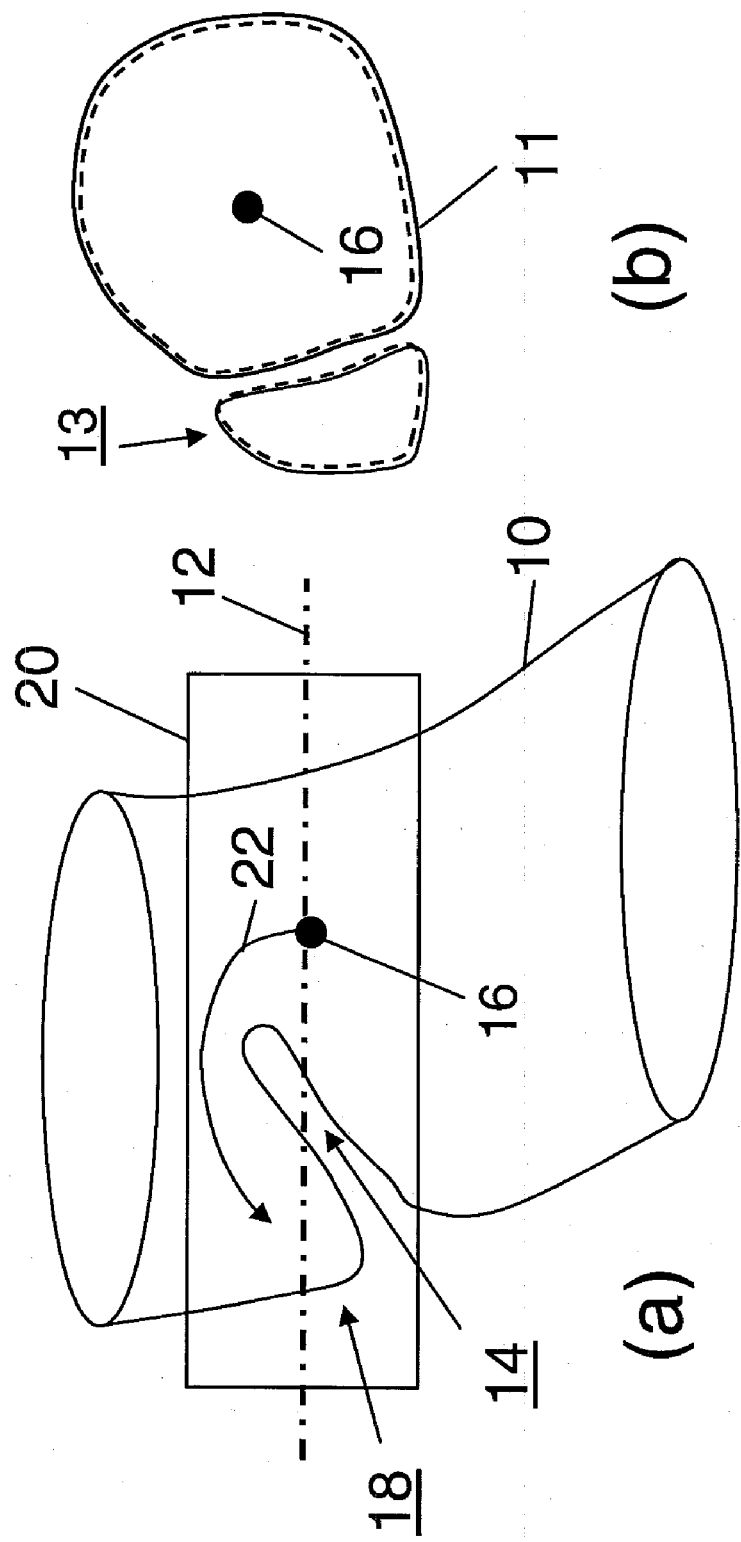
FIG. 2 shows an exemplary configuration in a virtual colonoscopy, including a Haustral fold, for illustrating seed growing in accordance with principles of the present invention.

In accordance with an exemplary embodiment of the present invention, as shown in FIG. 2, a three-dimensional (3D) region growing process of a suitable given thickness around focus point 16 is carried out, as indicated by colonic section 20 for the 3D region growing. In FIG. 2, the portion of the grown region that lies in the image plane 12, is then marked as seen. This region growing would "flood" the folds close by as indicated by the curved arrow line 22 to cause them to be marked as seen, for example at 13, but would not go into other loops that are not locally connected to the area of focus, as shown in FIG. 2. The thickness of the 3D region can be selected interactively or it can be calculated automatically based on surface characteristics.

Figure 6:
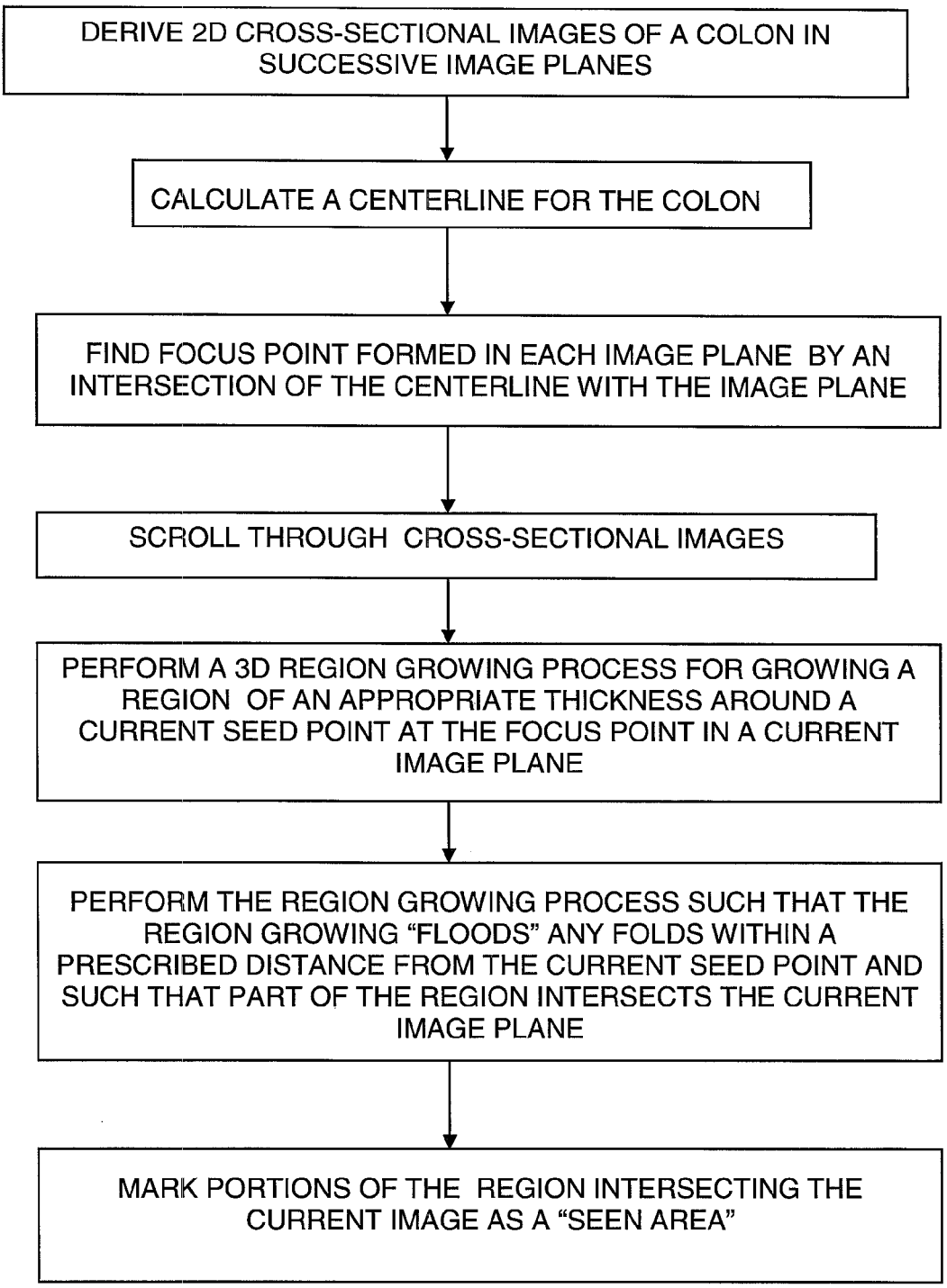
FIG. 6 shows a diagrammatic flow chart helpful in understanding principles of the present invention.

FIG. 6 shows a flowchart illustrating an example of the foregoing principle in accordance with the present invention, in which 2D cross-sectional images of a colon is derived in successive image planes; a centerline is calculated for the colon; a focus point is found in each image plane by an intersection of the centerline with the image plane; scrolling through the cross-sectional images is performed; a 3D region growing process is performed for growing a region of an appropriate thickness around a current seed point at the focus point in a current image plane; the region growing process is performed such that the region growing "floods" any folds within a prescribed distance from the current seed point and such that part of the region intersects the current image plane; and the regions which intersects the current image are marked as a "seen area".

Figure 3:
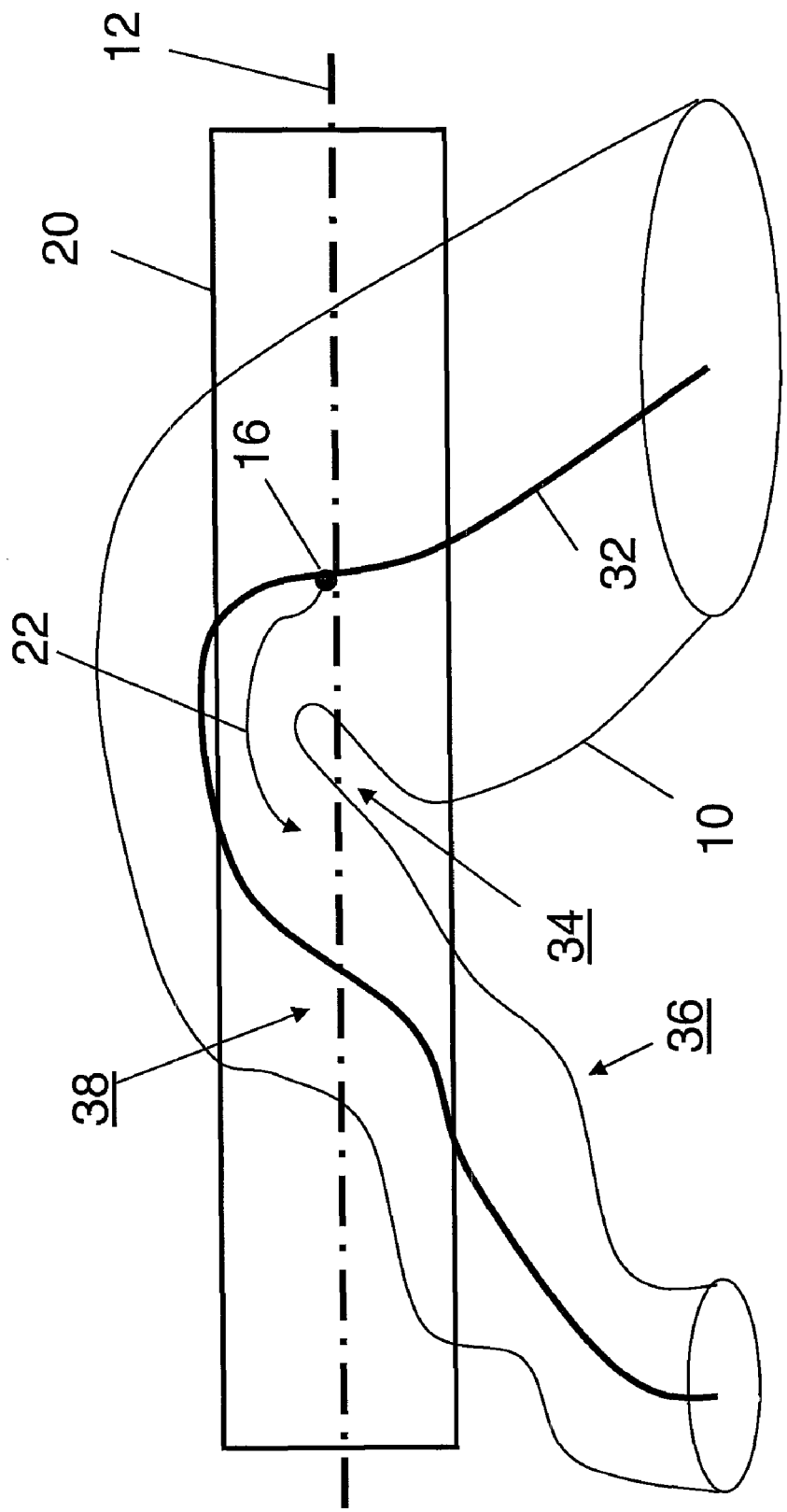
FIG. 3 shows a further exemplary configuration illustrating a typical problem solved in accordance with principles of the present invention.

It is herein recognized that special consideration needs to be given to the situation where a bend occurs in the colon, as shown in FIG. 3, which shows that, in this situation, a 3D region growing, as indicated by the curved arrow line 22, would fill a larger section 38 at a bend which should not be marked as seen at this point of the examination.

This occurrence can be avoided by different criteria in accordance with principles of the present invention, including not allowing such an undesirably marked region as seen if:

the intersection of the image plane with the 3D growing region growing contains a connected component 38 that does not contain the seed point and 38 contains another intersection with the centerline; or the area of 38 is larger than the area of the connected component containing the seed point.

The border is not added to the list of seen areas.

Figure 4:
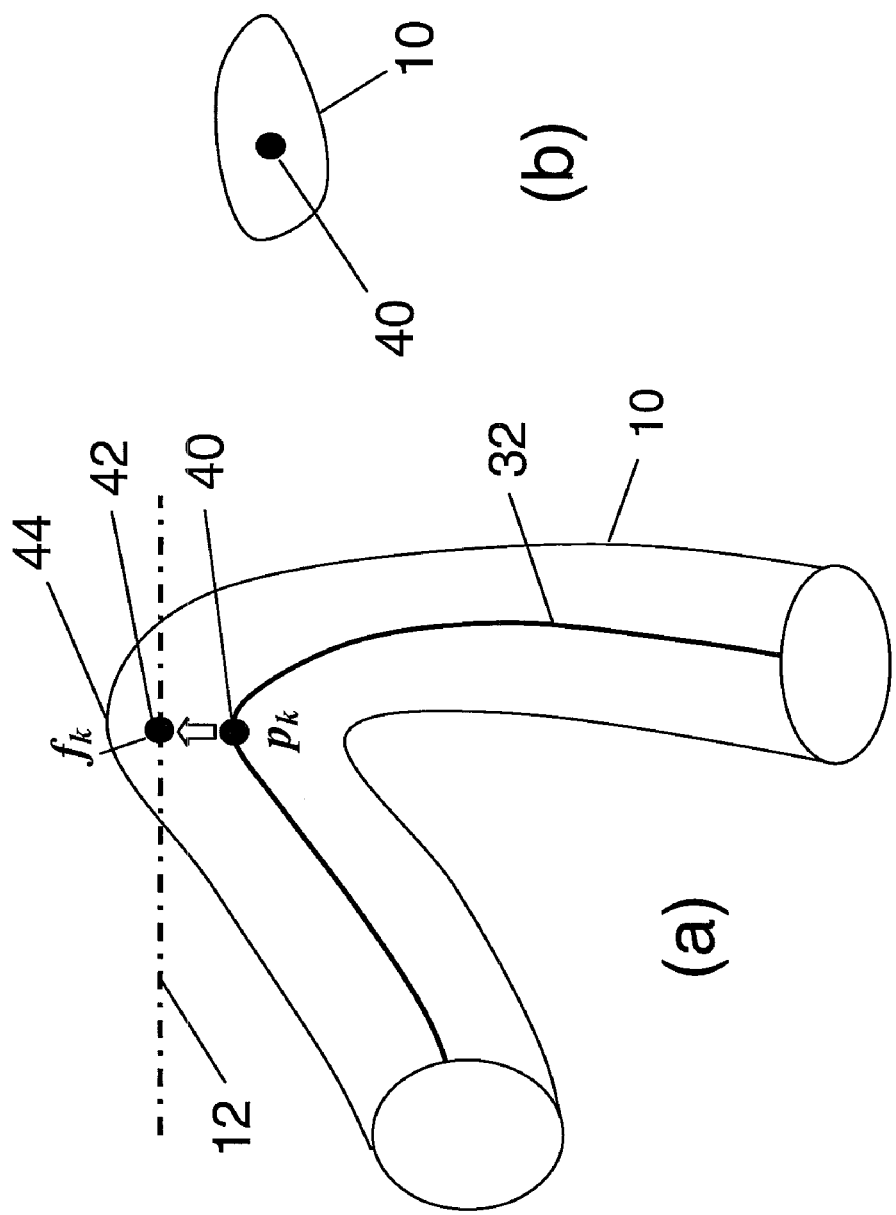
FIG. 4 shows a further exemplary configuration illustrating another typical problem solved using another embodiment in accordance with principles of the present invention.
Figure 5:
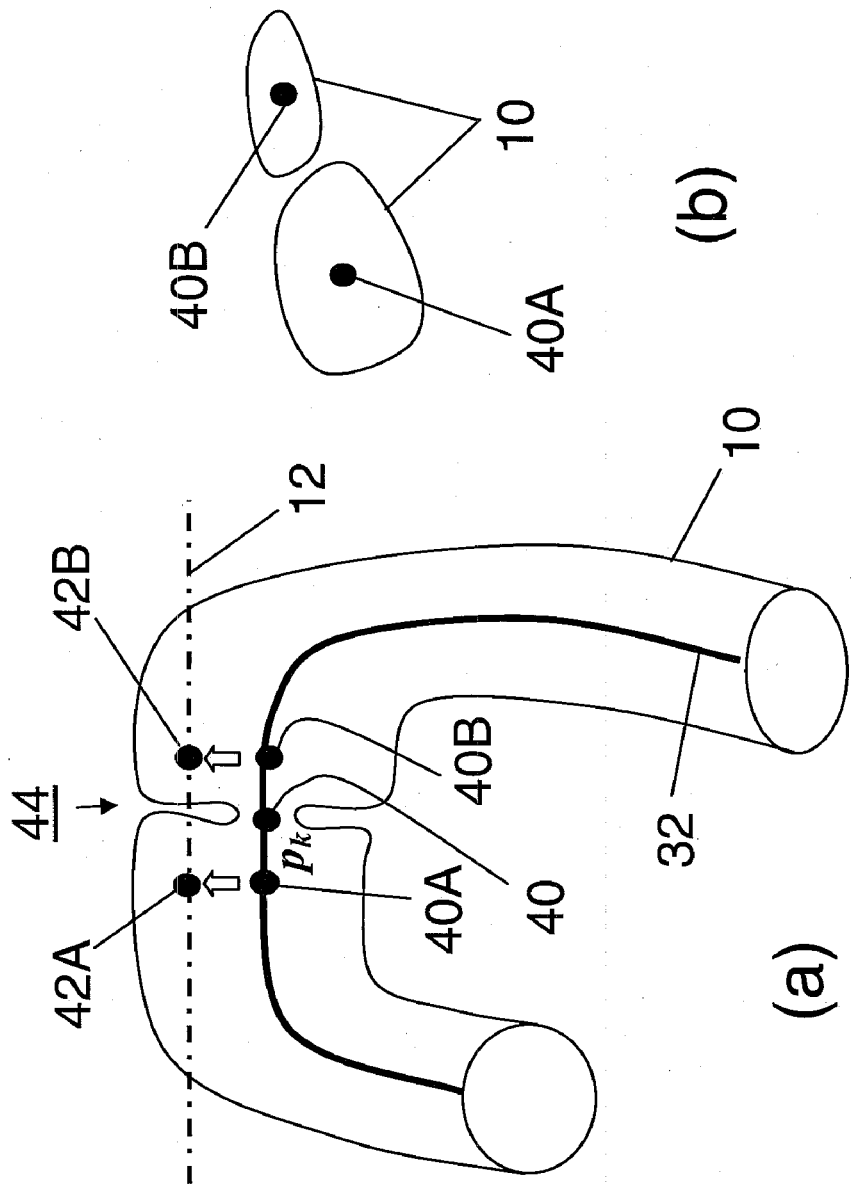
FIG. 5 shows a further embodiment in accordance with principles of the present invention.

The coverage of bends is provided for in accordance with principles of the present invention. As was disclosed in the aforementioned two patent applications of the present inventors, a user will be guided by a focus point that is shifted along the centerline; however at bends, the user has to move the plane away from the centerline in order to observe the complete surface. FIG. 4(a) shows a schematic illustration of a colon segment together with an axial cross-section corresponding to the location of the current image plane, or cutting plane, with a centerline 32 and, in FIG. (4b), an axial image showing a cross-section corresponding to image plane 12 which intersects the current centerline at 40. As FIG. 4 illustrates, the scroll direction should not be reversed as soon as the centerline changes course; instead, scanning should continue until the connected air component completely disappears form the axial images. This is especially important at a colonic flexure where the centerline makes a sharp turn, where reversing the scroll direction too soon would leave a significant area omitted from the inspection. In order not to lose the focus point for scrolling, a projection of the last centerline point into the image plane is used that remains visible as long as the area contains air. Thus, when no intersection point between the centerline and the current image plane is found, the centerline point $p_k$, at 40 is projected into the image plane as shown in FIG. 4 to form a projected point. The projected point becomes the new focal point $f_k$ at 42, as long as it does not collide with or penetrate the colon wall. As has been disclosed in the aforementioned prior patent applications, the focal points may be highlighted, for example in red, and serve as a guide throughout the navigation. These points will remain visible until the air component being observed fades away completely from the axial image. At that point, the scroll direction may be reversed without the risk of omitting areas from inspection. In the presence of a Haustral type fold at a critical point, it may happen that the focal point collides with the intruding fold. FIG. 5 illustrates such an instance where projecting centerline point $p_k$ is not sufficient to overcome the problem. In accordance with a principle of the invention, a number of centerline points surrounding $p_k$ are also projected into image plane 12. For example, in accordance with a principle of the invention, as shown in FIG. 5, the centerline point $p_k$ is split into a plurality of parts, e.g. two or more, such as at 40A and 40B, which are respectively projected into image plane 12 to form image points at 42A and 42B, upon the occurrence of a configuration such as that illustrated in FIG. 5.

The foregoing exemplary embodiments in accordance with the present invention are advantageously applied in combination with arrangements in accordance with steps of the methods disclosed by the present inventors in the aforementioned patent application Ser. No. 11/438,499 entitled METHOD AND SYSTEM FOR GUIDED TWO DIMENSIONAL COLON SCREENING wherein is described a method and system for guiding imaging reading for colon screening which includes scrolling through a succession of two dimensional (2D) cross-sectional images of a colon in respective image planes. A point of intersection with a current image plane with the centerline of the colon is marked in a first color in the current cross-sectional image. As the scrolling proceeds and a new current cross-sectional image in a respective image plane is observed, a new point of intersection is marked in the current cross-sectional image in the first color and the prior point of intersection is projected onto the new current cross-sectional image and marked in a second color.

The foregoing exemplary embodiments in accordance with the present invention are also advantageously applied in combination with arrangements in accordance with steps of the methods disclosed by the present inventors in the aforementioned patent application Ser. No. 11/438,617 entitled METHOD AND SYSTEM FOR DISPLAYING UNSEEN AREAS IN GUIDED TWO DIMENSIONAL COLON SCREENING, including steps for calculating segmentation and colon surface for a colon; calculating a centerline for the colon; designating as a current focus point a current point of intersection of a current portion of the centerline and a current cross-sectional image of a colon in a current image plane; and extracting a colon surface portion in a connected colon component containing the current focus point; and marking voxels of the colon surface portion as a "seen" area. Unseen areas of the colon surface are calculated by subtracting seen areas from the total colon area of observation. The unseen areas may then be displayed.

Reference is made to the two patents if further details of the methods disclosed therein are desired.

Figure 7:
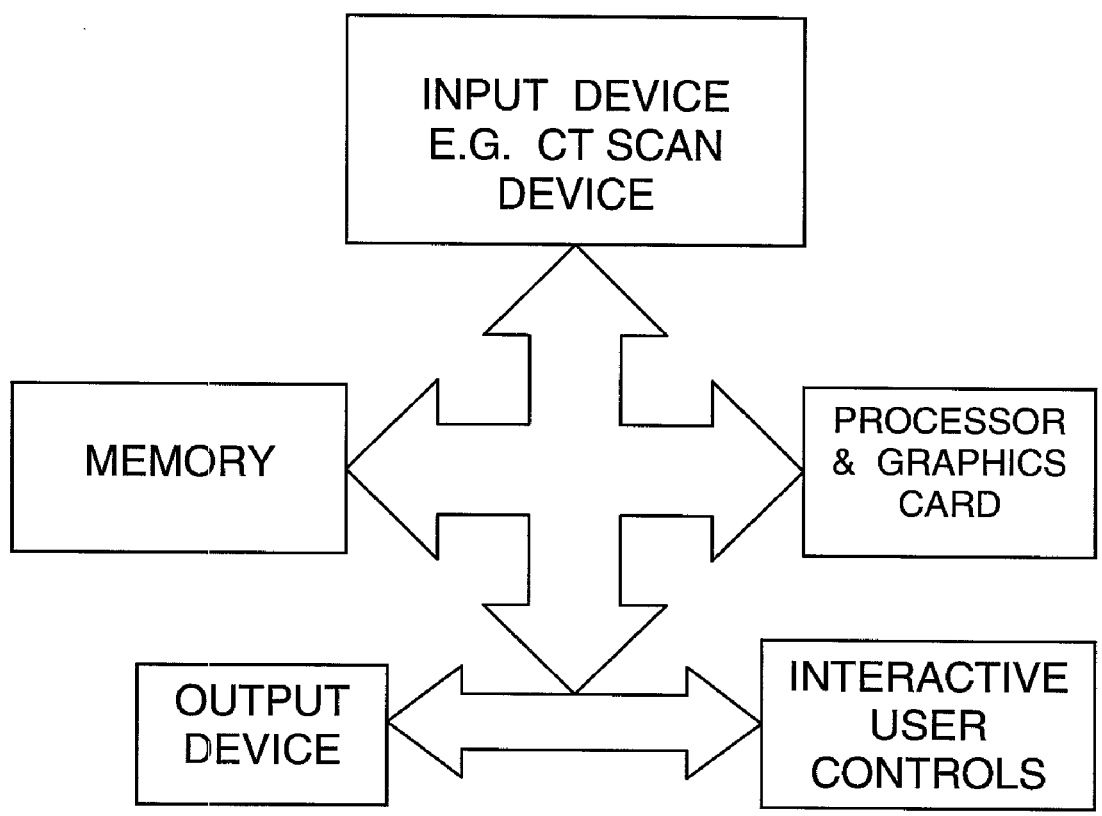
FIG. 7 shows the application of a programmed digital computer in an embodiment in accordance with principles of the present invention.

As will be apparent, the present invention is best intended to be implemented with the use and application of imaging equipment in conjunction with a programmed digital computer. FIG. 7 shows in basic schematic form a digital processor coupled for two way data communication with an input device, an output device, and a memory device for storing a program and other data. The input device is so designated in broad terms as a device for providing an appropriate image or images for processing in accordance with the present invention.

For example, the input may be from an imaging device, such as a device incorporated in a CATSCAN, X-ray machine, an MRI or other device, or a stored image, or by communication with another computer or device by way of direct connection, a modulated infrared beam, radio, land line, facsimile, or satellite as, for example, by way of the World Wide Web or Internet, or any other appropriate source of such data. The output device may include a computer type display device using any suitable apparatus such as a cathode-ray kinescope tube, a plasma display, liquid crystal display, and so forth, or it may or may not include a device for rendering an image and may include a memory device or part of the memory device of FIG. 7 for storing an image for further processing, or for viewing, or evaluation, as may be convenient, or it may utilize a connection or coupling including such as are noted above in relation to the input device.

The processor is operative with a program set up in accordance with the present invention for implementing steps of the invention. Such a programmed computer may interface readily through communications media such as land line, radio, the Internet, and so forth for image data acquisition and transmission.

The invention may be readily implemented, at least in part, in a software memory device and packaged in that form as a software product. This can be in the form of a computer program product comprising a computer useable medium having computer program logic recorded thereon for program code for performing the method of the present invention.

The present invention has also been explained in part by way of examples using illustrative exemplary embodiments. It will be understood that the description by way of exemplary embodiments is not intended to be limiting and that, while the present invention is broadly applicable, it is helpful to also illustrate its principles, without loss of generality, by way of exemplary embodiments.

It will also be understood that various changes and substitutions not necessarily herein explicitly described may be made by one of skill in the art to which it pertains. Such changes and substitutions may be made without departing from the spirit and scope of the invention which is defined by the claims following.

What is claimed is:

1. A method for guiding image reading for colon screening, comprising:
   calculating a centerline for a colon to be screened;
   scrolling through a succession of two dimensional (2D) cross-sectional images of a colon in respective image planes, such that a current image plane includes a respective current focus point formed by an intersection of said centerline with said current image plane;
   performing a three-dimensional (3D) region growing process for growing a region of a suitable given thickness around a current seed point in a current image plane, said current seed point being at said respective current focus point in said current image plane, such that said region growing floods any folds within a prescribed distance from said current seed point and such that part of said region intersects said current image plane; and
   marking portions of said region intersecting said current image with a first mark.

2. A method as recited in claim 1, wherein said step of performing a 3D region growing process comprises flooding Haustral fold areas within a given range of a respective current seed point.

3. A method as recited in claim 1, comprising:
   marking any of said portions marked with said first mark as "seen areas".

4. A method as recited in claim 3, comprising:
   calculating a total colon surface area by calculating segmentation and colon surface for said colon; and
   calculating unseen areas of said colon surface by subtracting said seen areas from said total colon area.

5. A method as recited in claim 1, comprising:
   marking as "not seen" any of said portions marked with said first mark that meet a given criterion, wherein said criterion comprises at least one of:
   (A) said region intersecting said given current image plane contains a further connected component not containing said current seed point, and contains a further intersection of said image plane with said centerline other than said current seed point, and
   (B) said further connected component exhibits a larger area than that exhibited by a connected component containing said current seed point; and marking remaining portions of said region intersecting said current image plane, not marked as "not seen", with a second mark as "seen areas".

6. A method as recited in claim 5, comprising:
calculating a total colon surface area by calculating segmentation and colon surface for said colon; and
calculating unseen areas of said colon surface by subtracting said seen areas from said total colon area.

7. A method as recited in claim 1, wherein said scrolling through a succession of two dimensional (2D) cross-sectional images of a colon in respective image planes comprises scrolling such that a current image plane includes a respective current focus point formed by an intersection of a projection of said centerline with said current image plane.

8. A method for guiding image reading for colon screening, comprising:
(a) calculating a centerline for a colon;
(b) scrolling through a succession of two dimensional (2D) cross-sectional images of a colon in respective image planes, such that a current image plane includes a respective current focus point formed by an intersection of said centerline with said current image plane;
(c) performing a three-dimensional (3D) region growing process for growing a region of a suitable given thickness around a current seed point in said current image plane, said current seed point being at said respective current focus point in said current image plane, such that said region growing "floods" folds within a prescribed distance from said current seed point such that part of said region intersects said current image plane;
(d) marking as "not seen" any portions of said region intersecting said current image plane that meet at least one of conditions (A) and (B), wherein:
(A) comprises said region intersecting said given current image plane containing a further connected component not containing said current seed point, and containing a further intersection of said image plane with said centerline other than said current seed point, and
(B) comprises said further connected component exhibiting a larger area than that exhibited by a connected component containing said current seed point; and
(e) marking remaining portions of said region intersecting said current image plane, not marked as "not seen", as "seen areas".

9. A method as recited in claim 8, wherein step (b) comprises scrolling such that a current image plane includes a respective current focus point formed by an intersection of a projection of said centerline with said current image plane.

10. A method as recited in claim 8, including:
(e') calculating a total colon surface area by calculating segmentation and colon surface for said colon; and
(e") calculating a total of unseen areas of said colon surface by subtracting said seen areas from said total colon area.

11. A method as recited in claim 8, wherein step (c) comprises flooding Haustral fold areas within a given range of a respective current seed point.

12. A method as recited in claim 8, wherein said step (b) comprises
scrolling through a succession of two dimensional (2D) cross-sectional images of a colon in respective image planes, such that a first current image plane includes a respective first current focus point formed by an intersection of said centerline with said first current cross-sectional image plane;
marking said first respective current focus point in a first color;
scrolling to a next current cross-sectional image plane in a respective next current image plane including a next respective current focus point;
marking said next respective current focus point in said first color;
projecting said first focus point onto said next current cross-sectional image to form a projection thereof; and
marking said projection in a second color.

13. A method for guiding image reading for colon screening, comprising:
calculating a centerline for a colon;
scrolling through a succession of two dimensional (2D) cross-sectional images of said colon in respective image planes, such that a current image plane includes a respective current focus point formed by an intersection of said centerline with said current image plane until, in the event of said colon exhibiting a bend such that said centerline exhibits a bend ahead of said scrolling, a critical image plane is reached, including a critical focus point, wherein further scrolling to a next plane causes said centerline to no longer intersect said next plane by veering away due to said bend;
projecting a guide line from said critical focus point in a substantially perpendicular direction to said critical image plane; and
scrolling through a further succession of 2D cross-sectional images of said colon in further respective image planes beyond said critical image plane, such that a further current image plane includes a further respective focus point formed by an intersection of said guide line with said further current image plane.

14. A method as recited in claim 13, wherein said step of scrolling through a further succession of 2D cross-sectional images comprises reversing the direction of scrolling once a wall of said colon is reached.

15. A method as recited in claim 13, wherein said step of projecting a guide line further comprises:
selecting an additional point on said centerline in the vicinity of said critical focus point and projecting an additional guide line from said additional point substantially perpendicularly to said critical image plane such that said further current image plane includes an additional focus point formed by an intersection of said additional guide line with said further current image plane.

16. A method as recited in claim 15, wherein said step of scrolling through a further succession of 2D cross-sectional images comprises reversing the direction of scrolling once a wall of said colon is reached.

17. A method as recited in claim 13, wherein said step of projecting a guide line comprises:
selecting a plurality of additional points on said centerline in the vicinity of said critical focus point and projecting additional respective guide lines from said additional points substantially perpendicularly to said critical image plane such that said further current image plane includes a plurality of additional focus points formed by respective intersections of said additional guide lines with said further current image plane.

18. A method as recited in claim 17, wherein said step of scrolling through a further succession of 2D cross-sectional images comprises reversing the direction of scrolling once a wall of said colon is reached.

19. A method as recited in claim 13, wherein said scrolling comprises:
  marking in a first color in a first current cross-sectional image said respective first current focus point;
  proceeding with said scrolling to a next successive current cross-sectional image in a respective next successive current image plane, said next successive current image plane exhibiting a next successive respective current focus point;
  marking said next successive respective current focus point in said first color;
  projecting said first focus point onto said next successive current cross-sectional image to form a projection thereof; and
  marking said projection in a second color.

20. A system for guiding image reading for colon screening, comprising:
  a memory device for storing a program and other data; and
  a processor in communication with said memory device, said processor being operative with said program to perform:
  (a) calculating a centerline for a colon;
  (b) scrolling through a succession of two dimensional (2D) cross-sectional images of a colon in respective image planes, such that a current image plane includes a respective current focus point formed by an intersection of said centerline with said current image plane;
  (c) performing a three-dimensional (3D) region growing process for growing a region of a suitable given thickness around a current seed point in a current image plane, said current seed point being at said respective current focus point in said current image plane, such that said region growing "floods" folds within a prescribed distance from said current seed point such that part of said region intersects said current image plane;
  (d) removing from consideration portions of said region intersecting said current image plane that meets at least one of conditions (A) and (B), wherein:
  condition (A) comprises said region intersecting said given current image plane containing a further connected component not containing said current seed point, and containing a further intersection of said image plane with said centerline other than said current seed point, and
  condition (B) comprises said further connected component exhibiting a larger area than that exhibited by a connected component containing said current seed point; and
  (e) marking remaining portions of said region intersecting said current image plane, not removed from consideration, as seen areas.

21. A system as recited in claim 20, wherein said processor is operative with said program to perform:
  (e') calculating a total colon surface area by calculating segmentation and colon surface for said colon; and
  (e") calculating unseen areas of said colon surface by subtracting said seen areas from said total colon area.

22. A system as recited in claim 20, wherein said step (b) comprises
  scrolling through a succession of two dimensional (2D) cross-sectional images of a colon in respective image planes, such that a first current cross-sectional image plane includes a respective first current focus point formed by an intersection of said centerline with said first current cross-sectional image plane;
  marking said first respective current focus point in a first color;
  scrolling to a next current cross-sectional image plane in a respective next current image plane including a next respective current focus point;
  marking said next respective current focus point in said first color;
  projecting said first focus point onto said next current cross-sectional image to form a projection thereof; and
  marking said projection in a second color.

23. A computer program product comprising a non-transitory computer useable medium having computer program logic recorded thereon for program code for guiding image reading for colon screening, comprising:
  (a) calculating a centerline for a colon;
  (b) scrolling through a succession of two dimensional (2D) cross-sectional images of a colon in respective image planes, such that a current image plane includes a respective current focus point formed by an intersection of said centerline with said current image plane;
  (c) performing a three-dimensional (3D) region growing process for growing a region of a suitable given thickness around a current seed point in a current image plane, said current seed point being at said respective current focus point in said current image plane, such that said region growing "floods" folds within a prescribed distance from said current seed point such that part of said region intersects said current image plane;
  (d) removing from consideration portions of said region intersecting said current image plane that meets at least one of conditions (A) and (B), wherein:
  condition (A) comprises said region intersecting said given current image plane containing a further connected component not containing said current seed point, and containing a further intersection of said image plane with said centerline other than said current seed point, and
  condition (B) comprises said further connected component exhibiting a larger area than that exhibited by a connected component containing said current seed point; and
  (e) marking remaining portions of said region intersecting said current image plane, not removed from consideration, as seen areas.

24. A computer program product as recited in claim 23, wherein said processor is operative with said program to perform:
  (e') calculating a total colon surface area by calculating segmentation and colon surface for said colon; and
  (e") calculating unseen areas of said colon surface by subtracting said seen areas from said total colon area.

25. A computer program product as recited in claim 23, wherein said step (b) comprises:
  scrolling through a succession of two dimensional (2D) cross-sectional images of a colon in respective image planes, such that a first current cross-sectional image plane includes a respective first current focus point formed by an intersection of said centerline with said first current cross-sectional image plane;
  marking said first respective current focus point in a first color;
  scrolling to a next current cross-sectional image plane in a respective next current image plane including a next respective current focus point;
  marking said next respective current focus point in said first color;
  projecting said first focus point onto said next current cross-sectional image to form a projection thereof; and
  marking said projection in a second color.

* * * * *